(12) United States Patent
Dershem et al.

(10) Patent No.: US 6,620,946 B2
(45) Date of Patent: Sep. 16, 2003

(54) LOW SHRINKAGE THERMOSETTING RESIN COMPOSITIONS AND METHODS OF USE THEREOF

(75) Inventors: Stephen M. Dershem, San Diego, CA (US); Kang Yang, San Diego, CA (US)

(73) Assignee: Loctite Corporation, Rocky Hill, CT (US)

( * ) Notice: Subject to any disclaimer, the term of this patent is extended or adjusted under 35 U.S.C. 154(b) by 0 days.

(21) Appl. No.: 10/137,064

(22) Filed: Apr. 30, 2002

(65) Prior Publication Data

US 2002/0188137 A1 Dec. 12, 2002

Related U.S. Application Data

(63) Continuation-in-part of application No. PCT/US01/30423, filed on Sep. 27, 2001.
(60) Provisional application No. 60/237,775, filed on Sep. 30, 2000.

(51) Int. Cl.⁷ .................. C07D 207/40; C07C 69/00
(52) U.S. Cl. ........................................ 548/545; 560/138
(58) Field of Search ........................... 560/138; 548/545

(56) References Cited

U.S. PATENT DOCUMENTS

| | | | |
|---|---|---|---|
| 5,723,066 A | 3/1998 | Coates et al. | |
| 6,229,020 B1 | 5/2001 | Shiono | |

*Primary Examiner*—Deborah C. Lambkin
(74) *Attorney, Agent, or Firm*—Stephen E. Reiter; Foley & Lardner

(57) ABSTRACT

In accordance with the present invention, there are provided thermosetting resin compositions with a reduced propensity to shrink in volume upon cure and methods of use therefor. The compositions of the present invention include compounds having aromatic, rigid-rod like spacer groups between the crosslinkable moieties. As such, these compounds impart a degree of liquid crystal-like character to the thermosetting resin composition which results in lower shrinkage upon cure. This effect follows from the well-known expansion that occurs when liquid crystal-like materials pass from a nematic liquid crystal-like state to an isotropic state. Further provided by the present invention are low shrinkage die attach pastes and methods of use therefor.

16 Claims, 1 Drawing Sheet

LOW SHRINKAGE THERMOSETTING RESIN COMPOSITIONS AND METHODS OF USE THEREOF

RELATED APPLICATIONS

This application is a continuation-in-part of PCT Application No. US01/30423 filed Sep. 27, 2001, which claims priority from U.S. Application No. 60/237,775 filed Sep. 30, 2000.

FIELD OF THE INVENTION

The present invention relates to thermosetting resin compositions and uses therefor. In particular, the present invention relates to compositions with markedly reduced shrinkage upon cure, thereby providing improved performance in adhesion applications. In a particular aspect, the present invention relates to die attach compositions useful for attaching semiconductor devices to carrier substrates.

BACKGROUND OF THE INVENTION

Thermosetting resins are commonly used in adhesive formulations due to the outstanding performance properties which can be achieved by forming a fully crosslinked (i.e., thermoset), three-dimensional network. These properties include cohesive bond strength, resistance to thermal and oxidative damage, and low moisture uptake. As a result, common thermosetting resins such as epoxy resins, bismaleimide resins, and cyanate ester resins have been employed extensively in applications ranging from structural adhesives (e.g., construction and aerospace applications) to microelectronics (e.g., die-attach and underfill applications).

Although thermosetting resins have been used successfully as adhesives in a variety of industries, a property inherent to all thermosetting resins which negatively impacts adhesion performance is shrinkage upon cure. This phenomenon is attributed to the formation of a three-dimensional, covalently crosslinked network during cure, which reduces intermolecular distances between the monomers used to form the crosslinked network. For example, before cure, the molecules which comprise the resin are separated by their characteristic van der Waal's radii. Upon cure, these intermolecular distances are reduced due to the formation of covalent bonds between monomers which produces the desired highly crosslinked thermoset material. This reduction of intermolecular distances creates internal stress throughout the thermoset network, which is manifested by reduced adhesion of the thermoset material to both the substrate and the object attached thereto.

It is well established that thermosetting monomers which cure via ring-opening chemistry (e.g., epoxies, benzoxazines) or ring-formation chemistry (e.g., cyanate esters) have reduced cure shrinkage. Ring-opening cure chemistry is advantageous since this physical transformation helps diminish volumetric shrinkage on cure. Similarly, ring-formation cure chemistry acts to reduce shrinkage due to the slight expansion which occurs upon ring-formation (much like that which occurs when water freezes to form ice crystals). Accordingly, epoxies, benzoxazines and cyanate esters all have excellent adhesive properties—presumably due to their diminished cure shrinkage. However, virtually all free-radically polymerized monomers do not participate in ring-opening or ring-forming reactions and therefore often exhibit severe cure shrinkage.

Strategies have been developed to address the problem of shrinkage upon cure. Common approaches include the addition of an inorganic filler to the adhesive formulation, and/or the use of a higher molecular weight thermosetting material. However, both of these strategies undesirably increase the viscosity of the final adhesive formulation. Accordingly, there remains a need for low shrinkage upon cure thermosetting resin compositions which do not detract from the properties of the adhesive formulation, in either its cured on uncured state, or its cure profile.

SUMMARY OF THE INVENTION

In accordance with the present invention, there are provided thermosetting resin compositions with a reduced propensity to shrink in volume upon cure and methods of use therefor. The compositions of the present invention include compounds having aromatic, rigid-rod like spacer groups between the crosslinkable moieties. As such, these compounds impart a degree of liquid crystal-like character to the thermosetting resin composition which results in lower shrinkage upon cure. This effect follows from the well-known expansion that occurs when liquid crystal-like materials pass from a nematic liquid crystal-like state to an isotropic state. Further provided by the present invention are low shrinkage formulations containing invention compounds and methods of use therefor.

DETAILED DESCRIPTION OF THE INVENTION

Figure 1:
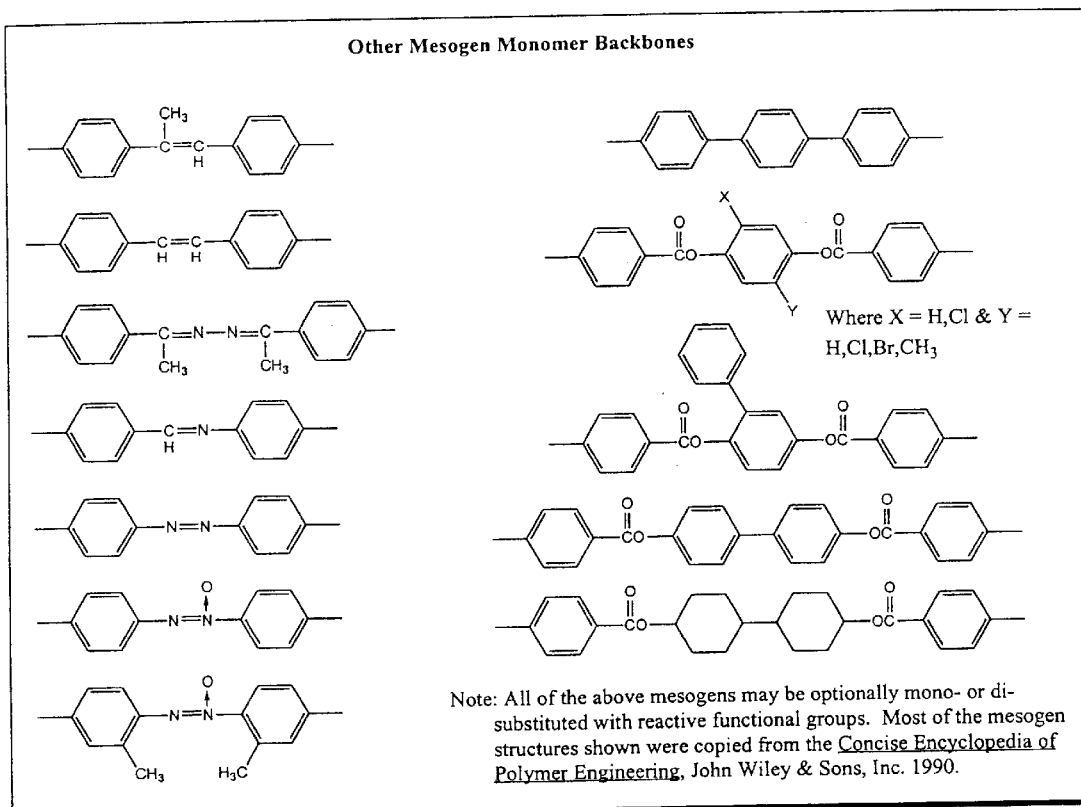
FIG. 1 illustrates several exemplary structures which can be incorporated into compounds contemplated by the present invention.

Thermosetting resin compositions of the present invention include compounds having the structure:

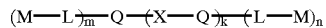

wherein:
each Q is independently substituted or unsubstituted phenylene, cyclohexylene, naphthylene, or heterocyclic,
X is optional and if present, is O, S, SO, $SO_2$, CO, $CO_2$ (in both orientations), $CO_3$, or $CR_2$ (wherein R is —H or substituted or unsubstituted lower alkyl), or substituted or unsubstituted lower heteroalkenylene,
L is optional and if present, is substituted or unsubstituted alkylene or oxyalkylene,
M is an ethylenically unsaturated crosslinkable moiety or saturated non-crosslinkable moiety,
n and m are each independently an integer between 0–3, provided that one of m and n is at least 1, and
k is 1 or 2.

As employed herein, the term "phenylene" refers to an optionally substituted, divalent 6-membered aromatic ring, the term "cyclohexylene" refers to an optionally substituted, divalent, saturated 6-membered ring, the term "naphthylene" refers to an optionally substituted, divalent 10 carbon fused aromatic ring system, and the term "heterocyclic" refers to optionally substituted, saturated or unsaturated, cyclic (i.e., ring-containing) groups containing one or more heteroatoms (e.g., N, O, S, or the like) as part of the ring structure, and having in the range of 3 up to 14 carbon atoms.

As employed herein, the term "lower alkyl" refers to straight or branched chain alkyl radicals having in the range of about 1 up to 4 carbon atoms.

As employed herein, the term "lower heteroalkenylene" refers to divalent, straight or branched chain spacer groups having in the range of about 1 up to 4 carbon atoms and/or heteroatoms, and wherein said spacer groups contain at least one double bond. Examples of such groups are illustrated in FIG. 1.

As employed herein, the term "heteroatom" refers to N, O, or S.

As employed herein, the term "substituted", when used in conjunction with any of the species referred to herein, includes substituents such as hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, oxo, amino, amido, succinimido, —C(O)H, acyl, oxyacyl, carboxyl, carbamate, sulfonyl, sulfonamide, sulfuryl, and the like.

As employed herein, the term "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkylene" refers to divalent, straight or branched chain alkyl groups containing in the range of about 1 to 20 carbon atoms.

As employed herein, "oxyalkylene" refers to divalent, straight or branched chain moieties which contain at least one oxygen atom within the hydrocarbon backbone.

As employed herein, the term "ethylenically unsaturated crosslinkable moiety" refers to a moiety which reacts with a curing catalyst under pre-determined curing conditions, wherein the moiety has at least one unit of ethylenic unsaturation. As employed herein, "ethylenic unsaturation" refers to a polymerizable (i.e., non-aromatic) carbon—carbon double bond, as shown below:

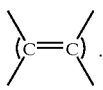

As employed herein, the term "saturated non-crosslinkable moiety" refers to hydrocarbon moieties which have no polymerizable double bonds, and therefore do not react with a curing catalyst under pre-determined curing conditions.

Preferred embodiments according to the present invention include compounds having the general structure set forth above, wherein Q is phenylene, m is 0, k is 1, and n is 1, resulting in compounds which have the structure:

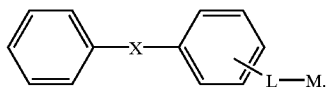

One embodiment according to the present invention includes compounds having the general structure set forth above, wherein X is O, L is methylene, and M is an ethylenically unsaturated crosslinkable moiety such as, for example, (meth)acrylate, resulting in compounds which have the structure:

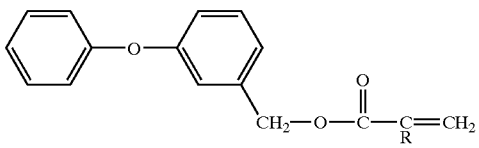

wherein R is —H or methyl.

Additional specific embodiments according to the present invention include compounds having the general structure set forth above, wherein Q is phenylene, X is absent, m is 0, and k is 1, resulting in compounds which have the following structures:

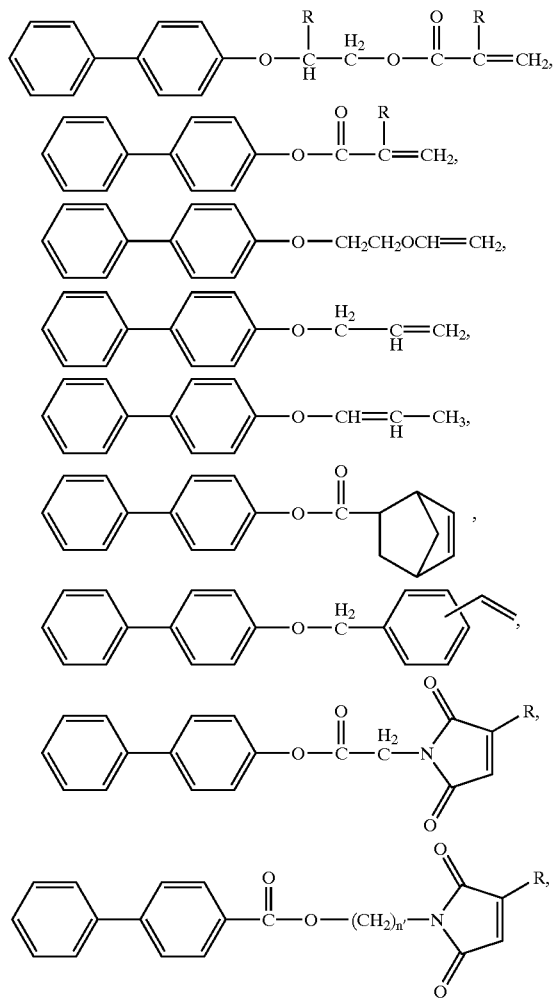

wherein R=H or CH$_2$ and n' is about 1 up to about 10.

While the substituents on the phenylene groups shown above are in the 1,4 positions, they may also occur at other positions on the phenylene ring, e.g., 1,2 or 1,3.

In an alternative embodiment, compounds contemplated for use in the practice of the present invention include compounds having the general structure set forth below

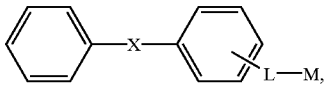

wherein X and L are as defined above and M is a saturated non-crosslinkable moiety.

Saturated moieties contemplated for use in the practice of the present invention include, for example, alkylcarboxylates, alkyl ethers, aryl ethers, and the like. As employed herein, the term "alkylcarboxylate" refers to moieties having the structure:

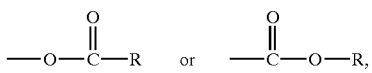

wherein R is an optionally substituted alkyl or cycloalkyl.

Specific embodiments contemplated according to this aspect of the present invention include compounds having the general structure set forth above, wherein Q is phenylene, X is absent, m is 0, n is 1, and k is 1, resulting in compounds having the structures set forth below:

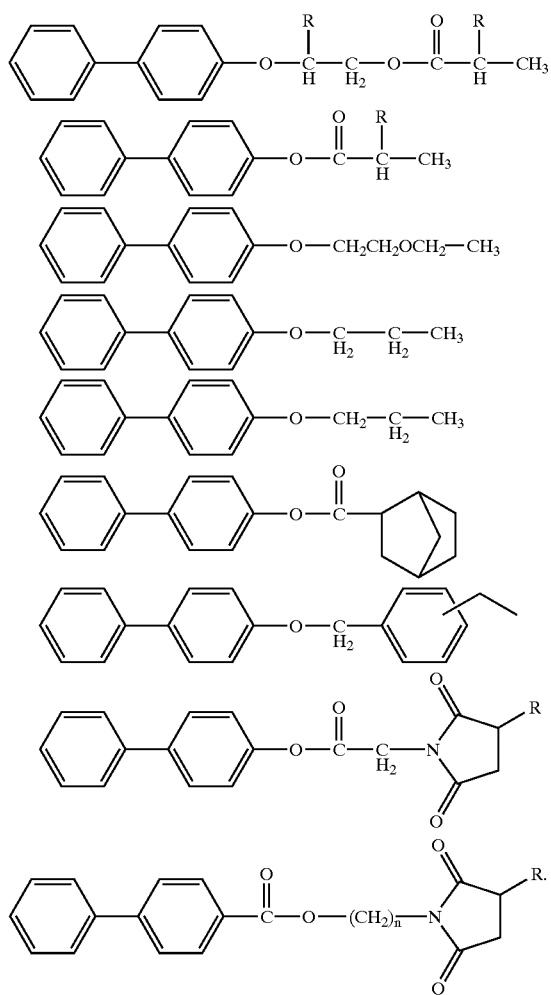

In addition to reduced shrinkage upon cure, the compounds contemplated for use herein provide further benefits when incorporated into a thermosetting resin composition. For example, the present compounds can be used to improve hydrophobicity of the resin and to reduce bleed on a variety of substrates, while maintaining low volatility of the overall composition.

In another aspect of the invention, the compositions of the present invention further include a maleimide, optionally a coupling agent, and a curing catalyst. Maleimides contemplated by the present invention have the structure:

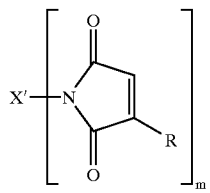

wherein:
m=1, 2, or 3,
each R is independently hydrogen or lower alkyl, and
X' is a monovalent moiety or a multivalent linking moiety.
Monovalent moieties or multivalent linking moieties are typically selected from (I) straight or branched chain alkyl, alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl, (II) siloxanes having the structure:

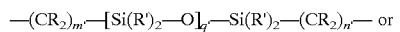

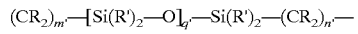

wherein
each R is independently defined as above, and each R' is independently selected from hydrogen, lower alkyl or aryl, m' falls in the range of 1 up to 10, n' falls in the range of 1 up to 10, and q' falls in the range of 1 up to 50, (III) polyalkylene oxides having the structure:

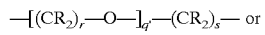

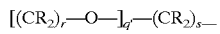

wherein each R is independently as defined above, r falls in the range of 1 up to 10, s falls in the range of 1 up to 10, and q' is as defined above, (IV) aromatic moieties having the structure:

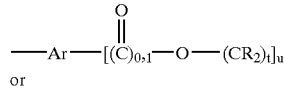
or

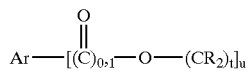

wherein each R is independently as defined above, t falls in the range of 2 up to 10, u is 1, 2 or 3, and Ar is as defined above, or

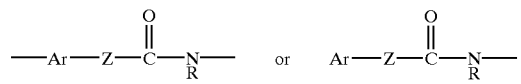

wherein
Z is O or NR, wherein R is hydrogen or lower alkyl,
(V) urethanes having the structure

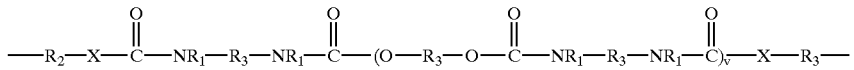

wherein:
each $R_1$ is independently hydrogen or lower alkyl,
each $R_2$ independently is an alkyl, aryl, or arylalkyl group having 1 to 18 carbon atoms;
$R_3$ is an alkyl or alkyloxy chain having up to about 100 atoms in the chain, which chain may contain aryl substituents;
X is O, S, N, or P; and
v is 0 to 50,
(VI) aromatic moieties having the structure:

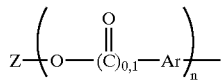

wherein
each Ar is a monosubstituted, disubstituted or trisubstituted aromatic or heteroaromatic ring having in the range of 3 up to about 10 carbon atoms,
n is 1 up to about 50, and
Z is selected from:
straight or branched chain alkyl, alkylene, oxyalkylene, alkenyl, alkenylene, oxyalkenylene, ester, or polyester, optionally containing substituents selected from hydroxy, alkoxy, carboxy, nitrile, cycloalkyl or cycloalkenyl,
siloxanes having the structure:

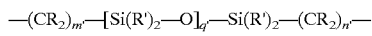

wherein
each R is independently defined as above, and each R' is independently selected from hydrogen, lower alkyl or aryl, m' falls in the range of 1 up to 10, n' falls in the range of 1 up to 10, and q' falls in the range of 1 up to 50,
polyalkylene oxides having the structure:

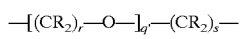

wherein each R is independently as defined above, r falls in the range of 1 up to 10, s falls in the range of 1 up to 10, and q' is as defined above,
aromatic moieties having the structure:

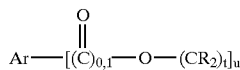

wherein each R is independently as defined above, t falls in the range of 2 up to 10, u is 1, 2 or 3, and Ar is as defined above,
as well as mixtures of any two or more thereof.

Preferred maleimides contemplated for use in the practice of the present invention are those which exist as liquids at ambient temperature. Presently preferred liquid maleimides include compounds wherein X' contains 12–500 carbon atoms. Most preferred liquid maleimides include compounds wherein X' contains 20–100 carbon atoms.

As employed herein, the term "cure initiator" refers to any chemical species which, upon exposure to sufficient energy (e.g., light, heat, or the like), catalyzes the crosslinking polymerization reaction which converts the functionalized monomeric compounds (contained within the overall composition) into a three-dimensional thermoset network. For example, when exposed to sufficient energy a free radical cure initiator decomposes into two parts which are uncharged, but which each possess at least one unpaired electron. Preferred as free radical initiators for use in the practice of the present invention are compounds which decompose (i.e., have a half life in the range of about 10 hours) at temperatures in the range of about 70 up to about 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-zobis (cyclohexanecarbonitrile)), and the like.

Peroxide initiators are presently preferred because they generate no gas release upon decomposition into free radicals. Those of skill in the art recognize, however, that in certain adhesive applications, the release of gas (e.g. $N_2$) during cure of the adhesive would be of no real concern. Generally in the range of about 0.2 up to 3 wt % of at least one free radical initiator (based on the total weight of the organic phase) will be employed, with in the range of about 0.5 up to 1.5 wt % preferred.

As employed herein, the term "coupling agent" refers to chemical species that are capable of bonding to a mineral surface and which also contain polymerizably reactive functional group(s) so as to enable interaction with the adhesive composition. Coupling agents thus facilitate linkage of the adhesive composition to the substrate to which it is applied.

Exemplary coupling agents contemplated for use in the practice of the present invention includes silicate esters, metal acrylate salts (e.g., aluminum methacrylate), titanates (e.g., titanium methacryloxyethylacetoacetate triisopropoxide), or compounds that contain a copolymerizable group and a chelating ligand (E.G., phosphine, mercaptan, acetoacetate, and the like). Generally in the range of about 0.1 up to about 10 wt % of at least one coupling agent (based on the total weight of the organic phase) will be employed, with in the range of about 0.5 up to about 2 wt % preferred.

Presently preferred coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention adhesive composition. Especially preferred coupling agents contemplated for use in the practice of the invention are oligomeric silicate coupling agents such as poly (methoxyvinylsiloxane).

In accordance with another aspect of the invention, invention compositions further include acrylate derivatives of oligomers of optionally substituted cyclopentadiene.

In accordance with still another aspect of the invention, there are provided formulations containing invention compounds. Such formulations can be used in a variety of applications, e.g., underfill, die attach, encapsulation, molding compounds, and the like. For example, when employed for the preparation of die-attach pastes, such formulations include:

in the range of about 10 up to about 80 wt % of the above-described adhesive composition, and in the range of about 20 up to about 90 wt % filler.

Fillers contemplated for use in the practice of the present invention can be electrically conductive and/or thermally conductive, and/or fillers having no appreciable conductivity, whose function is to primarily modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include fumed silica, alumina, titania, and the like.

In accordance with yet another embodiment of the present invention, there are provided assemblies of components adhered together employing the above-described adhesive compositions and/or die attach compositions. Thus, for example, assemblies including a first article permanently adhered to a second article by a cured aliquot of the above-described adhesive composition are provided. Articles contemplated for assembly employing invention compositions include memory devices, ASIC devices, microprocessors, flash memory devices, and the like.

Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In accordance with still another embodiment of the present invention, there are provided methods for adhesively attaching two component parts to produce the above-described assemblies. Thus, for example, a first article can be adhesively attached to a second article, employ a method comprising:

(a) applying the above-described adhesive composition to said first article, (b) bringing said first and second article into intimate contact to form an assembly wherein said first article and said second article are separated only by the adhesive composition applied in step (a), and thereafter, (c) subjecting said assembly to conditions suitable to cure said adhesive composition.

Similarly, a microelectronic device can be adhesively attached to a substrate, employing a method comprising:

(a) applying the above-described die attach paste to said substrate and/or said microelectronic device, (b) bringing said substrate and said device into intimate contact to form an assembly wherein said substrate and said device are separated only by the die attach composition applied in step (a), and thereafter, (c) subjecting said assembly to conditions suitable to cure said die attach composition.

Conditions suitable to cure invention die attach compositions comprise subjecting the above-described assembly to a temperature of less than about 200° C. for about 0.5 up to about 2 minutes. This rapid, short duration heating can be accomplished in a variety of ways, e.g., with an in-line heated rail, a belt furnace, or the like.

The invention will now be described in greater detail by reference to the following non-limiting examples.

EXAMPLE 1

Formulations were prepared from m-phenoxybenzyl acrylate (MPBA) which is an exemplary monomer according to the present invention and tricyclodecanedimethanol diacrylate (TCDDMDA) which was disclosed in U.S. Pat. No. 6,121,358. The structures of these monomers are shown below.

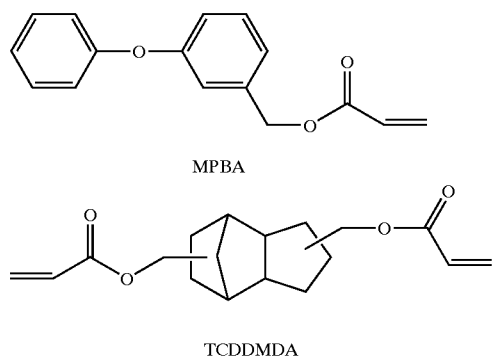

MPBA

TCDDMDA

Various mixtures of these two monomers (see Table 1) were catalyzed with 2 wt % dicumyl peroxide.

TABLE 1

Tensile Adhesion Test Compositions

| Formulation | 1a | 1b | 1c | 1d | 1e |
|---|---|---|---|---|---|
| MPBA | 73.5% | 83.3% | 88.2% | 93.1% | 98% |
| TCDDMDA | 24.5% | 14.7% | 9.8% | 4.9% | 0 |
| Dicumyperoxide | 2% | 2% | 2% | 2% | 2% |

The compositions were cured between clean copper slugs (1000×400×150 mils) and aluminum studs (290 mil head diameter) at 200° C. for twenty minutes. The assemblies were allowed to cool to room temperature and then tested for tensile strength using a Sebastian III tensile tester. The results of these tests are summarized in Table 2.

TABLE 2

Tensile Adhesion Test Results

Stud Pull Value (pounds force)

| Part | 1a | 1b | 1c | 1d | 1e |
|---|---|---|---|---|---|
| 1 | 25 | 43 | 0 | 94 | 71 |
| 2 | 14 | 36 | 92 | 106 | 77 |
| 3 | 26 | 38 | 93 | 105 | 78 |
| 4 | 27 | 38 | 87 | 58 | 67 |
| 5 | 0 | 53 | 83 | 86 | 43 |
| 6 | 0 | 32 | 64 | 72 | 74 |
| 7 | 13 | 48 | 61 | 112 | 74 |

TABLE 2-continued

Tensile Adhesion Test Results

Stud Pull Value (pounds force)

| Part | 1a | 1b | 1c | 1d | 1e |
|------|-----|------|------|------|------|
| 8 | 20 | 41 | 71 | 4 | 73 |
| 9 | 20 | 48 | 59 | 86 | 67 |
| 10 | 31 | 55 | 76 | 19 | 68 |
| Average | 17.6 | 43.2 | 68.6 | 74.2 | 69.2 |
| $\Sigma_{n-1}$ | 11 | 7.6 | 27 | 37 | 10 |

The adhesion increased for these mixtures as the concentration of MPBA in the mixture was raised. Without wishing to be bound by theory, it is believed that adhesion was improved with increasing MPBA because the shrinkage upon cure of the monomer mixtures was decreased. The TCDDMA is a highly reactive, relatively low equivalent weight, diacrylate monomer that exhibits considerable shrinkage upon cure.

The mixtures shown in Table 1 were not optimized for adhesion, but the results shown in Table 2 indicate that this approach has considerable potential. A more "fully formulated" system was prepared to further explore the use of the MPBA monomer. This test mixture was designated MV1258-13A and its composition is shown in Table 3.

TABLE 3

MV1258-13A Tensile Adhesion Test Compositions

| Component | Function | Percentage |
|-----------|----------|------------|
| X-Bismaleimide[1] | Co-monomer | 3.32 |
| MPBA | New (invention) co-monomer | 6.19 |
| Proprietary acrylate monomer[2] | Co-monomer | 6.20 |
| Ricon 130MA20[3] | Co-monomer | 1.00 |
| Silquest A-186[4] | Coupling Agent | 0.24 |
| QM-57[5] | Co-monomer | 2.40 |
| USP90MD[6] | Initiator | 0.65 |
| EA0018[7] | Silver flake filler | 40.0 |
| SF98[8] | Silver flake filler | 40.0 |

[1]Described in U.S. Pat. Nos. 6,034,194 and 6,034,195;
[2]U.S. patent pending (cycloaliphatic acrylate);
[3]Ricon Resins, Inc.;
[4]Osi Specialties;
[5]Rohm and Haas;
[6]Witco Corporation;
[7]Chemet Corporation;
[8]Degussa Corporation.

The MV1258-13A paste formulation was compared in a battery of tests to Ablestik 8360 (a widely used competitive die attach adhesive). The results of those tests are summarized in Table 4.

TABLE 4

Comparison of MV1258-13 and Ablestik 8360

| Metric | 1258-13 | Ablestik 8360 | Units |
|--------|---------|---------------|-------|
| 5 rpm Viscosity @ 25° C. | 10,076 | 7,618 | Centipoise |
| Thixotropic Index (0.5/5 rpm) | 6.18 | 5.81 | None |
| Potlife @ 25° C. | >24 | <24 | Hours |
| Adhesion on Ag plated Cu | | | |
| @ 25° C., Avg. (min.) | 96.8 (91.1) | 97.2 (77.1) | Kilograms force |
| @245° C., Avg. (min.) | 14.9 (11.6) | 8.1 (5.7) | Kilograms force |
| Adhesion on BTA-Cu | | | |
| @ 25° C., Avg. (min). | 84.1 (74.7) | 83.2 (27.7) | Kilograms force |
| @ 245° C., Avg. (min.) | 16.9 (12.3) | 7.6 (5.7) | Kilograms force |
| Adhesion on bar Cu | | | |
| @ 25° C., Avg. (min.) | 86.6 (80.8) | 86.3 (78.5) | Kilograms force |
| @ 245° C., Avg. (min.) | 20.8 (16.2) | 13.4 (8.9) | Kilograms force |
| 25° C. Adhesion after 1 min. @ 245° C. (wire bond simulation), Avg. (min.) | 88.2 (79.3) | 61.6 (49.1) | Kilograms force |
| Radius of Curvature (on Ag-Cu) | 0.44 ± 0.05 | 0.39 ± 0.04 | meters |
| Coefficient of Thermal Expansion | | | |
| below Tg | 45.8 | 52.0 | ppm/° C. |
| Above Tg | 156 | 170.0 | |
| Glass Transition Temperature | 29.4 | 16.9 | |
| Modulus of Elasticity @ 25° C. | 5.04 | 2.60 | GPa |
| Modulus of Elasticity @ 150° C. | 0.18 | 0.09 | GPa |
| Weight loss @ 250° C. (TGA) | 0.73 | 21.9 | % |
| Volume Resistivity | $9 \times 10^{-5}$ | $1.7 \times 10^{-4}$ | ohm-cm |
| Moisture Absorption (% wt. Gain) | | | |
| 24 hrs in 85/85 | 0.13 | 0.71 | % |
| 48 hrs in 85/85 | 0.13 | 0.86 | |
| 144 hrs in 85/85 | 0.13 | 0.87 | |
| 168 hrs in 85/85 | 0.13 | 0.85 | |

The MV1258-13A was found to have superior properties compared to the control paste. Even though the Ablestik 8360 had comparable room temperature die shear adhesion it was inferior at wire bond temperatures. It was also more seriously degraded by a one minute exposure to 245° C. (which was used to simulate real world wire bond conditions that would be required during the assembly process). Furthermore, the control material had much higher weight loss on cure and moisture absorption upon exposure to 85° C., 85% relative humidity moisture conditioning. The superior properties of the MV1258-13A were believed to be, in part, due to the use of the MPBA monomer.

While the invention has been described in detail with reference to certain preferred embodiments thereof, it will be understood that modifications and variations are within the spirit and scope of that which is described and claimed.

What is claimed is:

1. A compound having the following structure:

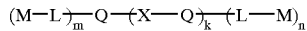

wherein:
  each Q is independently substituted or unsubstituted phenylene, cyclohexylene, or naphthylene,
  X is optional and if present, is O, S, SO, $SO_2$, CO, $CO_2$ (in both orientations), $CO_3$, or $CR_2$ (wherein R is —H or substituted or unsubstituted lower alkyl), or substituted or unsubstituted lower heteroalkenylene,
  L is optional and if present, is substituted or unsubstituted alkylene or oxyalkylene,
  M is an ethylenically unsaturated crosslinkable moiety or saturated non-crosslinkable moiety, n and m are each independently an integer between 0–3, provided that one of m and n is at least 1, and k is 1 or 2.

2. A compound according to claim 1 wherein M is a saturated non-crosslinkable moiety.

3. A compound according to claim 2, wherein M is an alkylcarboxylate, an alkyl ether, aryl ether, or a succinimide.

4. A compound according to claim 3, wherein M is an alkylcarboxylate.

5. A compound according to claim 1 wherein each O is phenylene, X is O, m is 0, L is not present, n is 1, and k is 1.

6. A compound according to claim 5 having the structure

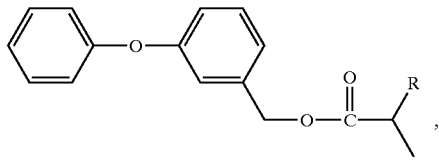

wherein R is hydrogen or optionally substituted alkyl.

7. A compound according to claim 5 having the structure

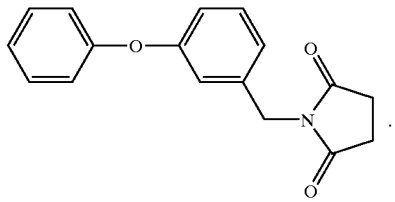

8. A low shrinkage adhesive composition comprising a compound according to claim 1 and a curing catalyst.

9. A low shrinkage thermosetting resin composition comprising:
   a) a compound according to claim 1,
   b) a maleimide,
   c) a coupling agent, and
   d) a cure initiator.

10. A method for reducing the shrinkage upon cure of a thermosetting resin composition, said method comprising combining the resin with a compound according to claim 1.

11. A method for improving adhesive strength of a thermosetting resin composition, said method comprising combining the resin with a compound according to claim 1.

12. A method for the preparation of a low shrinkage thermosetting resin composition, said method comprising combining the resin with a compound according to claim 1.

13. A compound according to claim 1 wherein X is O, L is methylene, and M is an ethylenically unsaturated crosslinkable moiety.

14. A compound according to claim 13 having the structure

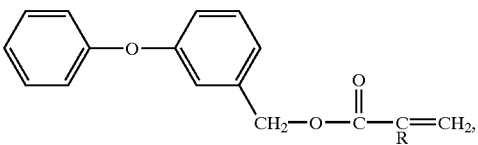

wherein R is —H or methyl.

15. A compound according to claim 1 wherein Q is phenylene, X is absent, m is 0, n is 1, and k is 1.

16. A compound according to claim 15 having the structure

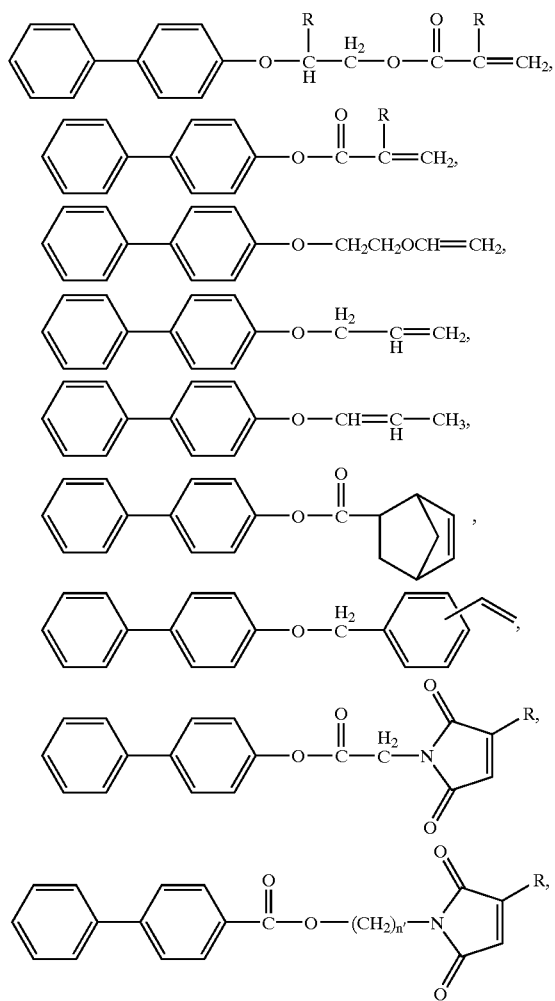

wherein R=H or $CH_3$.

* * * * *

UNITED STATES PATENT AND TRADEMARK OFFICE
CERTIFICATE OF CORRECTION

PATENT NO. : 6,620,946 B2 Page 1 of 1
DATED : September 16, 2003
INVENTOR(S) : Stephen M. Dershem and Kang Yang It is certified that error appears in the above-identified patent and that said Letters Patent is hereby corrected as shown below:

<u>Column 4,</u>
Line 55, after "n" delete the apostrophe

<u>Column 12,</u>
Line 23, in the "Units" column, insert -- °C --

<u>Column 13,</u>
Line 11, change "O" to -- Q --

Signed and Sealed this

Second Day of December, 2003

JAMES E. ROGAN
*Director of the United States Patent and Trademark Office*